(12) United States Patent
Sagripanti

(10) Patent No.: US 7,838,227 B1
(45) Date of Patent: Nov. 23, 2010

(54) SIMULTANEOUS DETECTION OF BIOLOGICAL AGENTS BY SOLID-STATE HYBRIDIZATION AND NAKED EYE VISUALIZATION

(75) Inventor: Jose-Luis Sagripanti, BelAir, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 643 days.

(21) Appl. No.: 11/546,741

(22) Filed: Oct. 12, 2006

Related U.S. Application Data

(60) Provisional application No. 60/730,166, filed on Oct. 24, 2005.

(51) Int. Cl.
*C12Q 1/68* (2006.01)
*C07H 21/04* (2006.01)
*C12P 19/34* (2006.01)

(52) U.S. Cl. .......................... 435/6; 536/24.3; 435/91.2

(58) Field of Classification Search ....................... None
See application file for complete search history.

(56) References Cited

U.S. PATENT DOCUMENTS 5,573,913 A * 11/1996 Rosemeyer et al. ............ 435/6

OTHER PUBLICATIONS

Wilson, W.J., et al. Sequence specific identification of 18 pathogenic microorganisms using microarray technology. 2002. Molecular and Cellular Probes. vol. 16 pp. 119-127.*

Quere, Ronan et al. White spot syndrome virus and infectious hypodermal and hematopoietic necrosis virus simulatneous diagnosis by miniarray system with colorimetry detection. 2002. Journal of Virological Methods vol. 105 pp. 189-196.*

* cited by examiner

*Primary Examiner*—Stephen Kapushoc
*Assistant Examiner*—Amanda Shaw
(74) *Attorney, Agent, or Firm*—Ulysses John Biffoni

(57) ABSTRACT

The invention relates to methods and products simultaneously enabling detection of several biological threat agents, including viruses and bacteria, during a combat situation or in any suspected contamination situation.

14 Claims, 8 Drawing Sheets

Examples of Capture Nucleic Acids

Figure 4:
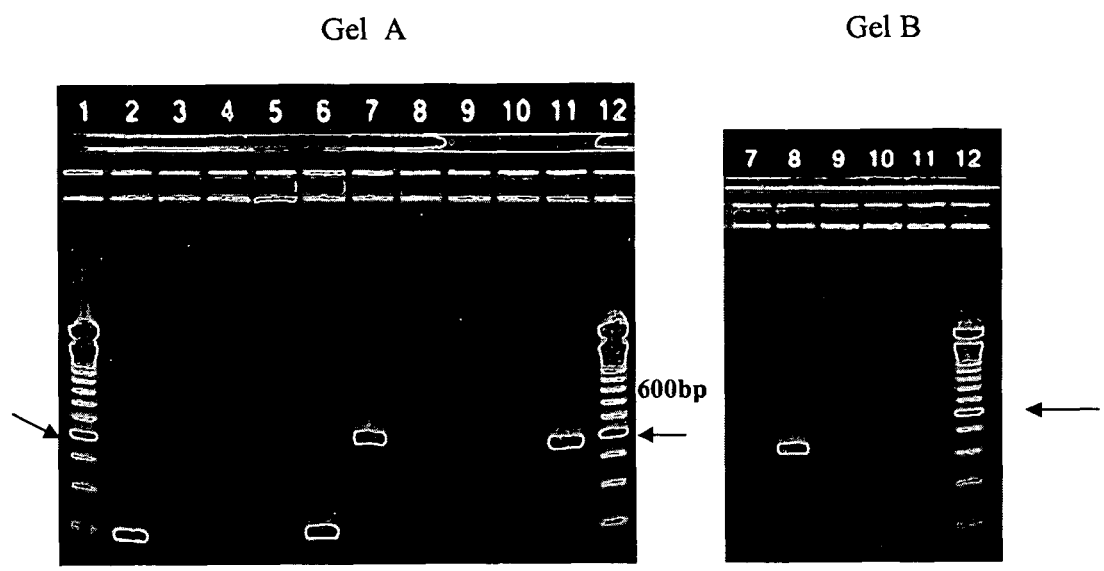

| Name | Sequence | Specificity | SEQ ID NUMBER |
|---|---|---|---|
| OPHA1 | ttgttatgagtgcttggtataaggagcc | Orthopoxvirus | SEQ ID NUMBER:1 |
| OPHA2 | caattccagatgatgtacttactgtagtgtatgag | Orthopoxvirus | SEQ ID NUMBER:2 |
| OPHA3 | caatacttttgttactaatatcattagtat | Orthopoxvirus | SEQ ID NUMBER:3 |
| OPTK1 | ataatcggccccatgttttcagg | Orthopoxvirus | SEQ ID NUMBER:4 |
| OPTK2 | ggctactataactattttccttcgtttgcc | Orthopoxvirus | SEQ ID NUMBER:5 |
| HA-COW | ctacacatacatctaaaaaaatagg | Cowpox | SEQ ID NUMBER:6 |
| HA-CML | tgataaagaagaagatcatacagtc | Camelpox, Monkeypox, Vaccinia | SEQ ID NUMBER:7 |
| HA-VAC | tcctcagacatctaaaaaaatagg | Vaccinia, Monkeypox | SEQ ID NUMBER:8 |
| HA-VAR | tcctcagacacagatatctaaaaa | Variola, Camelpox | SEQ ID NUMBER:9 |
| HA-VAR-2 | tcattagtatactctacaccttatcctcagacacagatatctaaaaaaat | Variola | SEQ ID NUMBER:10 |
| HA-VAR-3 | tatattatttctactacatgatagagttgcatcatcacctattttttag | Variola | SEQ ID NUMBER:11 |
| cM3W | acatraankgngtngtrtcraanccdaycc | Alphavirus | SEQ ID NUMBER:12 |
| M2W-A | yagagcdttttcgcaystrgc | Alphavirus | SEQ ID NUMBER:13 |
| VEE-1 | tgatcgaaacggaggtggacccatccga | VEE | SEQ ID NUMBER:14 |
| WEE-1 | tcattgagagcgaagtcgaccgggacca | WEE | SEQ ID NUMBER:15 |
| EEE-1 | tcattgagggagaagtggatacagacca | EEE | SEQ ID NUMBER:16 |
| FMV-1 | ttatagaaagcgaagtcgaccgggaaca | FMV | SEQ ID NUMBER:17 |
| SIN-1 | taatcgagctggaggttcctaccacagc | SIN | SEQ ID NUMBER:18 |

FIG. 1

Examples of Capture Nuclei Acids

| Name | Sequence | Specificity | SEQ ID NUMBER |
|---|---|---|---|
| PAG_1F476_501 | tggatttcaagttgtactggaccgat | *B. anthracis* pXO1 | SEQ ID NUMBER:19 |
| PAG_1R600_625 | tgtcacggtctggaaccgtaggtcca | *B. anthracis* pXO1 | SEQ ID NUMBER:20 |
| CAPB_1F954_977 | tgctgaccaatctaagcctgcgtt | *B. anthracis* pXO2 | SEQ ID NUMBER:21 |
| CAPB_1R1097_1122 | agcaaactgctcagtacgatcaacgc | *B. anthracis* pXO2 | SEQ ID NUMBER:22 |
| IRP1_1F5788_5813 | acccacctcattggctatggcggcgt | *Yersinia* group | SEQ ID NUMBER:23 |
| IRP1_1R5962_5987 | tcacgcgggatgtgatactccggcgt | *Yersinia* group | SEQ ID NUMBER:24 |
| CAPB_1F356_381 | agccacttttgcaatcgctgtgtgag | *Francisella tularensis* | SEQ ID NUMBER:25 |
| CAPB_1R560_585 | agctgcgattagttctgagcctcggt | *Francisella tularensis* | SEQ ID NUMBER:26 |
| WCBQ_1F21_46 | tgccattgccctgtcatttgccgcag | *Burkholderia* group | SEQ ID NUMBER:27 |
| WCBQ_1R255_280 | acaactgactgaacagactcaggtcg | *Burkholderia* group | SEQ ID NUMBER:28 |
| EEEV_1F10_31 | ttacttgtctgcggcgccttgg | Eastern Equine Enc. virus | SEQ ID NUMBER:29 |
| EEEV_1R1_1 | taggctcctccccacat | Eastern Equine Enc. virus | SEQ ID NUMBER:30 |
| BMEI1877_1F60_85 | cgatggcgtcatccatgtgctgggtg | *Brucella* group | SEQ ID NUMBER:31 |
| BMEI1877_1R364_389 | agtttgagcatgatgccgacgaaagc | *Brucella* group | SEQ ID NUMBER:32 |
| ECS0540_1F574_599 | gcaggcctgaactcatcgtcggatga | *Escherichia coli* O157:H7 | SEQ ID NUMBER:33 |
| ECS0540_1R898_923 | tcatcccaatacgagcggtcgctggt | *Escherichia coli* O157:H7 | SEQ ID NUMBER:34 |
| VAR_1F182615_182640 | gcagcaccgtatacaccacccaatgg | Variola virus | SEQ ID NUMBER:35 |
| VAR_1R182969_182994 | acgtctccaacagacgtgtgtccgga | Variola virus | SEQ ID NUMBER:36 |
| MAR_1F835_861 | acactacatcctttggtgcggacctc | Marburg virus | SEQ ID NUMBER:37 |
| MAR_1R1225_1250 | tttctcgtttctggctgaggacggc | Marburg virus | SEQ ID NUMBER:38 |
| RIFM_1F2675_2700 | gggttcagttagcctctcactggacg | Rift Valley Fever virus | SEQ ID NUMBER:39 |
| RIFM_1R3092_3117 | aggcggcatcacaagatacggctgct | Rift Valley Fever virus | SEQ ID NUMBER:40 |
| YEL_12_1F40_64 | tggcagccatcaaaagggtggaatg | Yellow Fever virus | SEQ ID NUMBER:41 |
| YEL_14_1R15_39 | tccaatcagtgatccgcacagcttg | Yellow Fever virus | SEQ ID NUMBER:42 |
| HEN_1F649_674 | agtgactgctccagatacagccgagg | Hendra virus | SEQ ID NUMBER:43 |
| HEN_1R1135_1160 | tgttgagagcacccatggatcggtcg | Hendra virus | SEQ ID NUMBER:44 |
| CBU_1551_1F337_361 | cccaacgaaaccttgcgtgaggcat | Coxiella burnetti | SEQ ID NUMBER:45 |
| CBU_1551_1R621_646 | aaacgtctcgcttaaactcaacgacg | Coxiella burnetti | SEQ ID NUMBER:46 |
| RP293_1F | gcttattttagaggttatagagttcg | Rickettsia group | SEQ ID NUMBER:47 |
| RP293_1R | acttcttgaggtaaaagtaaagctc | Rickettsia group | SEQ ID NUMBER:48 |

FIG. 2

Expected Amplicon Sizes

| PCR Primer Pair | Specificity | Approximate Size of Amplicon (bp)[a] |
|---|---|---|
| OPHA1, OPHA2 | Orthopoxviruses | 576 |
| OPHA2, OPHA3 | Orthopoxviruses | 697 |
| OPTK1, OPTK2 | Orthopoxviruses | 297 |
| HA-VAR-2, HA-VAR-3 | variola virus | 90 |
| cM3W, M2W-A | Alphaviruses | 431 |

FIG. 3

Amplified Target Nucleic Acids Using a Single Set of Primers

Detection of Biological Threat Agents In a Sample

Strip A

| | |
|---|---|
| Neg. Ctr. | Neg. Ctr. |
| VEE-1 | OPHA-1 |
| WEE-1 | cM3W |
| EEE-1 | HA-VAC |
| FMV-1 | HA-VAR |
| SIN-1 | HA-COW |
| Neg. Ctr. | HA-CML |
| Neg. Ctr. | Neg. Ctr. |

Strip B

| | |
|---|---|
| Neg. Ctr. | Neg. Ctr. |
| VEE-1 | OPHA-1 |
| WEE-1 | cM3W |
| EEE-1 | HA-VAC |
| FMV-1 | HA-VAR |
| SIN-1 | HA-COW |
| Neg.Ctr. | HA-CML |
| Neg. Ctr. | Neg. Ctr. |

FIG. 6

Detection of Biological Threat Agents in a Sample

| Strip C | | Strip D | |
|---|---|---|---|
| Neg. Ctr. | Neg. Ctr. | Neg. Ctr. | Neg. Ctr. |
| VEE-1 | OPHA-1 | VEE-1 | OPHA-1 |
| WEE-1 | cM3W | WEE-1 | cM3W |
| EEE-1 | HA-VAC | EEE-1 | HA-VAC |
| FMV-1 | HA-VAR | FMV-1 | HA-VAR |
| SIN-1 | HA-COW | SIN-1 | HA-COW |
| Neg. Ctr. | HA-CML | Neg. Ctr. | HA-CML |
| Neg. Ctr. | Neg. Ctr. | Neg. Ctr. | Neg. Ctr. |

FIG. 7

Detection Strips Produced with a Macroarray Printing Tool

| | |
|---|---|
| Neg. Ctr. | Neg. Ctr. |
| OPHA-1 | VEE-1 |
| cM3W | WEE-1 |
| HA-VAC | EEE-1 |
| HA-VAR | SIN-1 |
| HA-COW | FMV-1 |
| HA-CML | Neg. Ctr. |
| Neg. Ctr. | Neg. Ctr. |

FIG. 8

SIMULTANEOUS DETECTION OF BIOLOGICAL AGENTS BY SOLID-STATE HYBRIDIZATION AND NAKED EYE VISUALIZATION

RELATED APPLICATION

This application claims the benefit of priority from U.S. provisional application Ser. No. 60/730,166, filed on Oct. 24, 2005.

GOVERNMENTAL INTEREST

The invention described herein may be manufactured, used, and licensed by or for the United States Government.

FIELD OF THE INVENTION

This invention relates to methods and products enabling simultaneously detection of several biological threat agents, including viruses and bacteria, during combat or in suspected contaminated samples or locations. The present invention allows the detection of one or more biological threat agents by selective binding of such agents to a solid substrate and inspecting generated color patterns preferably by eye.

BACKGROUND OF THE INVENTION

With terrorist activity increasing new technologies are being developed enabling the detection of biological threat agents both in combat and civilian environments. Current detection methods identifying biological threat agents, such as viruses and bacteria, use ELISA (enzyme linked immunological assay) and PCR (polymerase chain reaction, based on nucleic acid amplification) as operative core platforms. Such detection methods work well in hospitals or other medical institutions but are not as well suited for biodefense applications, such as detecting biological threat agents during combat or in compromised environments. ELISA and other antibody-based methods relay on stable antibodies and enzymes, which have low stability after deployment and therefore do not last long during combat or during long transports to suspected compromised areas. PCR methods require thermal cyclers, energy supply sources, and a large logistic footprint that either consumes resources needed in other tasks or sensitive equipment that is not easy to transport.

In addition, ELIZA and PCR based detection methods are limited in that they are not able to detect multiple threat agents at once, particularly under conditions encountered in combat or a threat situation. One is able to detect several virus types using PCR, but the amount of virus types that can be detected at once is limited by the number of fluorochromes that are available for differentiating. In addition, PCR multiplexing techniques are generally expensive and required delicate equipment that is not easily transported. PCR multiplexing is costly, complex, and does not function well to analyze the massive amounts of agent present after a biological attack.

SUMMARY OF THE INVENTION

Accordingly, it is an object of the present invention to meet the foregoing needs by providing detection methods and products capable of detecting one or more biological threat agents simultaneously located in a suspect sample and in a simple and cost effective manner. The suspect sample may be obtained from a combat location or a civilian threat location. The methods and products of the present invention preferably enable the identification of one or more biological threat agents by simple visual inspection of the detection means. The products and methods of the present invention can be easily performed without extensive training of an operator, complex equipment, or vast logistic support. The operator of the methods and devices of the present invention are preferably soldiers having little or no training in microbiology or virology.

One embodiment of the present invention is a method of detecting a biological threat agent comprising the steps of
  a) extracting target nucleic acid from a suspect sample taken from a combat situation;
  b) labeling said target nucleic acid with a probe;
  c) attaching said target nucleic acid to capture nucleic acid wherein said capture nucleic acid is located on specific locations on a solid substrate; and
  d) reading the presence or absence of a biological threat agent.

The target nucleic acid may be amplified by polymerase change reaction using primers sets selected from SEQ ID NOS 1 through 48. The biological threat agent may be selected from the group consisting of an alphavirus, orthopoxvirus, filovirus, bunyavirus, flavivirus, paramyxovirus, *Bacillus anthracis, Yesinia pestis, Francicella tularensis, Brucellas, E. coli* 0157:H7, *Burkholderias, Coxiella, Rickettsias*, or a combination there of. The reading may consist of a visual inspection by eye. The probe may be selected from the group consisting of visible, UV, IR fluorescent, radioactive, mass, and electrochemical labels. It is preferred that the probe is digoxigenin. The capture nucleic acid may be selected from the group consisting of SEQ ID NOS: 1-48.

Another embodiment of the present invention is a method of detecting a biological threat agent comprising the steps of:
  a) extracting target nucleic acid from a suspect sample taken from a combat situation;
  b) attaching said target nucleic acid to capture nucleic acid wherein said capture nucleic acid is located on specific locations on a solid substrate;
  c) labeling said target nucleic acid with a probe; and
  d) reading the presence or absence of said biological threat agent.

The target nucleic acid may be amplified by polymerase change reaction using primers sets selected from SEQ ID NOS 1 through 48. The biological threat agent may be selected from the group comprising an alphavirus, orthopoxvirus, filovirus, bunyavirus, flavivirus, paramyxovirus, *Bacillus anthracis, Yesinia pestis, Francicella tularensis, Brucellas, E. coli* 0157:H7, *Burkholderias, Coxiella, Rickettsias*, or a combination there of. The reading may consists of a visual inspection by eye. The probe maybe selected from the group consisting of visible, UV, IR fluorescent, radioactive, mass, and electrochemical labels. The probe is preferably digoxigenin. The capture nucleic acid is selected from the group consisting of SEQ ID NOS: 1-48.

Another embodiment of the present invention is a method of detecting a biological threat agent comprising the steps of:
  a) extracting target nucleic acid from a suspect sample taken from a combat situation;
  b) labeling said target nucleic acid with a chromatic substance;
  c) attaching said target nucleic acid to capture nucleic acid wherein said capture nucleic acid is located on specific locations on a solid substrate; and
  d) reading by visual inspection of the solid support by eye the presence or absence of said biological threat agent.

The target nucleic acid may be amplified by polymerase chain reaction using primers sets selected from SEQ ID NOS 1 through 48. The biological threat agent may be selected from the group consisting of an alphavirus, orthopoxvirus, filovirus, bunyavirus, flavivirus, paramyxovirus, *Bacillus anthracis, Yesinia pestis, Francicella tularensis, Brucellas, E. coli* 0157:H7, *Burkholderias, Coxiella, Rickettsias*, or a combination thereof. The reading may consists of a visual inspection by eye. The visual inspection by eye is preferably of colors on the solid substrate. The capture nucleic acid maybe selected from the group consisting of SEQ ID NOS: 1-48.

BRIEF DESCRIPTION OF THE INVENTION

FIG. 1 Examples of capture nucleic acids of the present invention.

FIG. 2 Examples of capture nucleic acids of the present invention.

FIG. 3 Expected Amplicon Size. Though the present invention is intended to be used in a civilian threat, or combat situation, to detect biological threat agents in a suspect sample, the present invention was developed in laboratories so that biological threat agents could be handled safely. Consequently, oligonucleotides described in FIG. 1 and FIG. 2 were used to amplify target nucleic acid regions of biological threat agents. The oligonucleotides were shown to amplify nucleic acid regions of the correct size (i.e., based on the number of base pairs "bp").

FIG. 4 Amplified target nucleic acids were prepared in the laboratory using a single set of primers and a sample containing one biological threat agent.

As of observed on Gel A, PCR primers OPHA1 and OPHA2 (SEQ ID #1 and SEQ ID #2) in lanes 7 and 11, or OPTK1 and OPTK2 (SEQ ID #4 and SEQ ID #5) in lanes 2 and 6, for amplification of all orthopoxvirus sequences were used with DNA and RNA obtained from vaccinia virus cultures (lanes 2, 6, 7, 11), FMV cultures (lanes 3 and 8), Vero cell conditioned media (lanes 4 and 9) and BHK cell conditioned media (lanes 5 and 10). DNA fragments of the correct size 297 by and 576 by were amplified only from the vaccinia virus samples with primers (SEQ ID #4 and SEQ ID #5) specific for the TK gene (lanes 2 and 6) and for primers SEQ ID #1 and SEQ ID #2 for the HA gene (lanes 7 and 11). Amplification occurred in the presence (lanes 2 and 7) or the absence (lanes 6 and 11) of AMV reverse transcriptase. The size of amplification products was estimated by comparison to samples of a 100 by DNA ladder (InVitrogen Corporation, Carlsbad, Calif.) in lanes 1 and 12.

As observed on Gel B, PCR primers (SEQ ID #12 and SEQ ID #13) for amplification of all alphaviruses NSP-1 gene sequences were used with DNA and RNA obtained from vaccinia virus (lane 7), FMV (lane 8), Vero cell conditioned media (lane 9), BHK conditioned media (lane 10). Product of the correct size (app. 431 bp) was amplified only from the FMV sample in the presence (lane 8) but not the absence (lane 11) of AMV reverse transcriptase. The size of amplification products was estimated by comparison to samples of a 100 by DNA ladder (InVitrogen Corporation, Carlsbad, Calif.) in lane 12, where the brighter band in the middle of the markers is 600 by in length (indicated by the arrows) and each band is 100 by apart in size.

Figure 5:
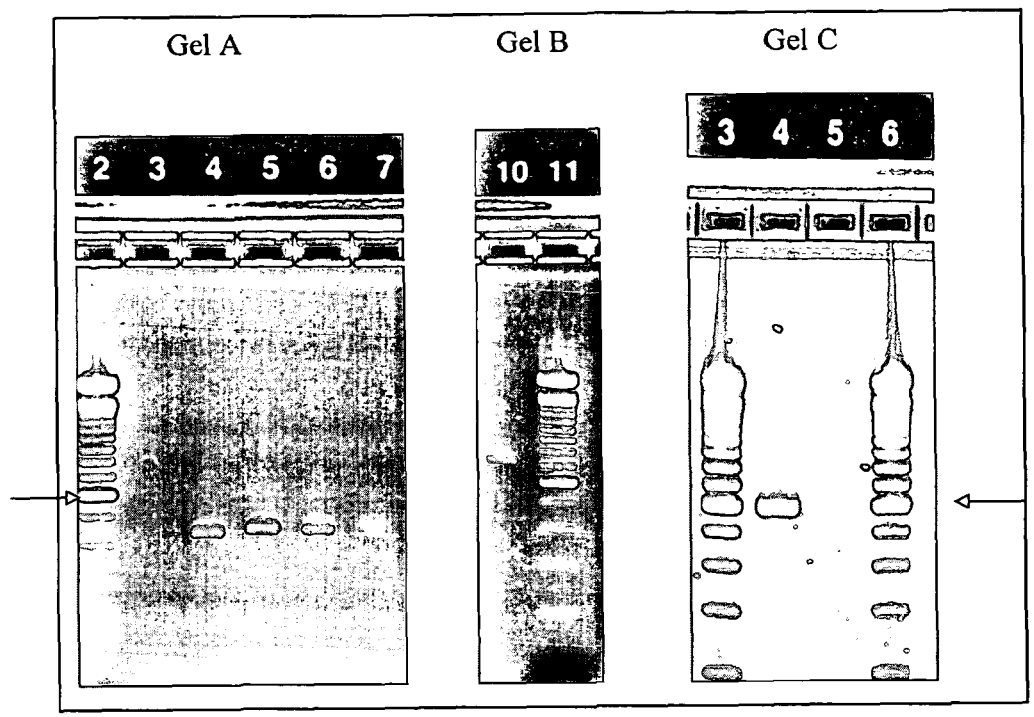

FIG. 5 Amplified target nucleic acids prepared in the laboratory using more than one set of primers and a sample containing more than one biological threat agents (Multiplexing).

Multiplex PCR amplification of several alphaviruses and vaccinia virus. RT-PCR reactions included primers OPHA2 (SEQ ID NO: 2) and OPHA3 (SEQ ID NO: 3) for amplification of orthopoxvirus sequences and primers cM3W (SEQ ID NO: 12) and M2W-A (SEQ ID NO: 13) for amplification of alphavirus sequences.

As observed on Gel A, RT-PCR amplification of alphavirus sequences from FMV (lane 4), SIN (lane 5), WEE (lane 6), VEE (lane 7) were of the expected 431 by size. Amplification was not observed with the negative control (lane 3). The negative control was sterile distilled water, instead of target DNA sampled in the corresponding wells. The lack of signal with the negative controls assures low background and further supports specificity. No amplification products corresponding to the size of the orthopoxvirus amplicon (697 bp) were observed in any alphavirus lanes.

As observed on Gel B, amplification of orthopoxvirus sequences from vaccinia virus (lane 10) corresponded to the expected 697 by size. No amplification product corresponding to the size of the alphavirus amplicon was observed. The size of amplification products was estimated by comparison to samples of a 100 by DNA ladder (InVitrogen Corporation, Carlsbad, Calif.) in lanes 2 and 11.

As observed on Gel C, RT-PCR reactions included primers OPHA1 (SEQ ID NO:1) and OPHA2 (SEQ ID NO: 2) for amplification of orthopoxvirus sequences and primers cM3W (SEQ ID NO: 12) and M2W-A (SEQ ID NO: 13) for amplification of alphavirus sequences were used to amplify a region of the orthopoxvirus nucleic acid sequence of 576 by when using vaccinia virus DNA as substrate (lane 4) and a product with a nucleic acid sequence of 431 by for alphavirus amplification using FMV RNA as substrate (lane 5). A 100 by DNA ladder was added in lanes 3 and 6 to estimate the size of amplification products.

FIGS. 6 & 7 Detection of biological threat agents in a sample. Nucleic acid (target nucleic acid) of biological threat agents were amplified and labeled with digoxigenin (DIG) corresponding to vaccinia (Strip A), VEE (Strip B), and variola (Strip C and Strip D). The placement of capture oligonucleotides is indicated on the array. Macroarray strips were produced by the spot blot technique and the placement of capture oligonucleotides is indicated on the array. The macroarray strips were hybridized to the amplified digoxigenin labeled Variola target nucleic acid at 40° C. (Strip C) and 35° C. (Strip D). Vaccinia virus target nucleic acid bound only the generic orthopoxvirus capture oligonucleotide, OPHA-1 (SEQ ID NO: 1), and the vaccinia specific oligonucleotide, HA-VAC (SEQ ID NO: 8). VEE PCR product bound (produced with primers SEQ ID #12 and SEQ ID #13) to only the generic alphavirus capture oligonucleotide, cM3W (SEQ ID NO: 12), and the VEE specific oligonucleotide, VEE-1 (SEQ ID NO: 14). Since variola was not available (the deadly virus is kept in only two repositories, at CDC and Russia), a 90-bp fragment of variola DNA, was synthesized using PCR by joining 2 variola sequences, each 50 oligonucleotides long and produced with a 10-base overlap at their 3' ends (using sequences SEQ ID #10 and SEQ ID #11). This synthetic variola stimulant bound only to the variola specific capture oligonucleotide, HA-VAR (SEQ ID NO: 9). The synthetic variola fragment does not include the area corresponding to the generic orthopoxvirus oligonucleotide, OPHA-1. The microarray strips (membranes) shown in FIGS. 6 and 7 were taken under white light. The SID corresponding to the capture primers indicated in the figure correspond to the ID numbers listed in FIG. 1. All the PCR amplification products were labeled with Digoxigenin (DIG) and all membranes were spotted with capture oligos, all in the same scheme, and days in advance. One strip was dipped in each sample containing one specific virus. Each virus made a spot with the corresponding probe as indicated by the dot in the corresponding location without overlapping, cross reacting, or false positives. The negative control (labeled Neg. Ctr. in the membrane) is distilled water processed identically as a sample containing target DNA.

FIG. 8 Detection of biological threat agents using a solid support wherein a macroarraying printing tool was used to place capture nucleic acid on the solid support. To improve the uniformity of spots on a macroarray, a macroarray printing tool was used. RT-PCR products amplified from Sindbis virus with Primers SEQ ID #12 and SEQ ID #13 bound to spots corresponding only to the generic alphavirus oligonucleotide, cM3W (SEQ ID NO: 12), and the Sindbis virus specific oligonucleotide, SIN-1 (SEQ ID NO: 18). Spots on the microarray strips (membranes in this figure) produced with the macroarray printing tool appeared to be much more uniform in size and shape than spots on the earlier strips (FIGS. 6 and 7).

DETAILED DESCRIPTION OF THE INVENTION

Reference will now be made to preferred embodiments of this invention, examples of which will be obvious from the detailed description of the invention. The present invention relates to methods and products in which one or more biological threat agents may be identified in a combat or civilian threat situation. In order to better understand the invention the following terms have been defined:

"Biological Threat Agent" shall mean a biological entity that is a threat to life including virus and bacteria, for example.

"Capture Nucleic Acid" is a nucleic acid, RNA or DNA, derived from a biological threat agent and attached to a solid support.

"Combat Situation" is any situation requiring biodefense such as army combat or a terrorist attack wherein biological threat agents are implemented and require detection.

"EEE" is Eastern Equine Encephalitis Virus

"FMV" is Fort Morgan Virus

"SIN" is Sinbis Virus, a common and well studied Alphavirus

"Suspect Sample" is a sample thought to contain a biological threat agent.

"Target Nucleic Acid" is a nucleic acid, RNA or DNA, derived from a biological threat agent from a suspect sample.

"VEE" is Venezuelan Equine Encephalitis.

"WEE" is Western Equine Encephalitis Virus

Capture Nucleic Acid

One element of the present invention is a capture nucleic acid, that is, a nucleic acid sequence, such as an oligonucleotide, capable of binding to the nucleic acid (RNA or DNA) of one or more biological threat agent of the same group or family. It is preferred that the capture nucleic acid bind to one or more members of the orthopox- or alpha-virus families. More preferably, it binds specifically to nucleic acids of alphaviruses, including Venezuelan equine encephalitis, or nucleic acid from each of orthopoxviruses, including variola virus (VAR). Examples of capture nucleic acid sequences used in the present invention are illustrated in FIG. 1 and FIG. 2 including SEQUENCE ID NUMBERS 1 through 44. SEQ ID 1 will hybridize to any Orthopoxvirus (Orthopoxyiridae family), which includes variola-smallpox, camelpox, monkeypox, cowpox, and other related viruses. SEQ ID 1 will not hybridize to non-Orthopoxvirus.

Other capture nucleic acid may bind to whole pathogenic families including, but not limited to, orthopoxviruses, arenaviruses, filoviruses, flaviviruses, hantaviruses, and other threat viruses, or members of the *Bacillus, Yersinia, Francicella, Burkholderia, Brucella, Escherichia, Rickettsia,* or *Coxiella* genera and other pathogenic bacteria. Examples of specific oligos and their specificity are listed in FIGS. 1 and 2. For example, a cM3W oligonucleotide was used as a capture nucleic acid to bind to any alphaviral sequence to detect an alphviral biological threat agent. Also, generic to all alphaviruses, oligonucleotides cM3W and M2W-A (SEQ ID 12 and SEQ ID #13) to the NSP-1 gene were used as a capture nucleic acid in the present invention. The sequence of the NSP-1 gene used as a capture nucleic acid were identified by examination of an alignment of the NSP-1 gene of several alphaviruses including two (2) strains of VEE, two (2) strains of WEE, one (1) strain of Eastern equine encephalomyelitis virus (EEE), one (1) strain of FMV, one (1) strain of SIN, one (1) strain of Buggy Creek virus, and one (1) strain of Kyzylagach virus. Additional oligonucleotides ID 14 to 18 were used to capture specific viruses of interests.

Oligonucleotides (SEQ ID #1, SEQ ID #2) used as a capture nucleic acid for orthopoxvirus sequences were identified by alignment to the thymidine kinase gene (SEQ ID #4 and SEQ ID #5) or to the hemahglutinin gene (SEQ IDS #1, #2 and #3) sequences that are conserved in all orthopoxviruses.

In addition probes SEQ ID #9 and SEQ ID #11 were used to selectively capture variola DNA. Although probe (SEQ ID #10) was mainly used as a simulant for virulent variola virus, due to its size, it performed very well capturing variola sequences. Moreover, capture nucleic acids, SEQ IDS #6, #7, and #8 captured additional specific orthopoxviruses.

Additional oligonucleotide sequences of capture probes (SEQ ID #19 through SEQ ID #48) were used to identify bacteria: *Bacillus anthracia, Yersinia* species, *Francisella tularensis, Burkholderia* species, *Brucella* species, *Escherichia coli* O157:H7; *Coxiella burnettii, Rickettsia* species and viruses: Variola virus, Marburg virus, Eastern Equine Encephalitis virus, Rift Valley fever virus, Yellow fever virus, and Hendra virus.

Capture nucleic acid that are oligonucleotides may be chemically synthesized and may have a size of, between 7 and 300 bases long, and more preferably a length between 20 and 50 bases. This invention will help in detecting, or excluding, the presence of biological threat agents in a variety of samples, specifically powders and other environmental samples of interest in biodefense applications.

Binding Capture Nucleic Acid to a Solid Support

Capture nucleic acid may be attached to solid supports by several approaches. The preferred approach is by crosslinking the capture nucleic acid to a solid support such as a membrane (usually by baking or UV exposure). Alternatively, capture nucleic acid may be bound to a surface by affinity. For example, binding of negatively charged capture nucleic acid to a positively charge surface, such as ionic exchange materials, affinity materials, silica, positively charged membranes, or positively charged columns. Also, capture nucleic acid may be labeled with a generic ligand to a membrane coated with the generic ligand's ligant. For example, by binding capture nucleic acid labeled with Avidin to a membrane coated with streptavidin, or vice versa.

Target Nucleic Acid

Another element of the present invention is a target nucleic acid. A target nucleic acid sequence may be a complete DNA sequence of biological threat agent, or a complete RNA sequence of a gene found in a biological threat agent. A target nucleic acid sequence may also be an amplified product of a DNA or RNA sequence of a biological threat agent as shown in FIG. 4 and FIG. 5 for example. A target nucleic acid sequence may be extracted from a suspect sample containing one or more biological threat agents in a combat and/or civilian threat situation. FIG. 5 demonstrates the amplification of multiple target sequences that have been extracted from a sample containing one or more biological threat agent(s). Typically, in such suspect samples, larges amounts of biological threat agents are present so that the intact target nucleic acid may be extracted from the suspect sample at the site where the suspect sample is located, and without amplification of the target nucleic acid sequence.

Methods of extracting target nucleic acid from biological threat agents include organic extraction (e.g., phenol:chloroform) followed by ethanol precipitation.

Another method of extracting target nucleic acid used in the present invention includes the use of beads as follows (reference 1): Extraction buffer (100 ml of 100 mM Tris-HCl [pH 8.0], 100 mM sodium EDTA [pH 8.0], 1.5 M NaCl) is mixed with 100 g (wet weight) of soil. Glass beads (100 g, Bio-Spec Products, Bartesville, U.S.) are added and the sample blended in a Bead-Beater (Bio-Spec Products) for 2 minutes. Sodium dodecyl, sulphate (SDS) is added (10 ml; 20%) and blending continued for a further 5 sec. The sample is incubated at 65° C. for 1 hr, transferred to centrifuge bottles (250 ml) and centrifuged at 6000 g for 10 min. The supernatant is collected, and the soil pellet re-extracted with further extraction buffer (100 ml), incubation at 65° C. for 10 minutes and centrifugation as above. Supernatants are transferred to centrifuge tubes (50 ml) containing a half-volume of polyethylene glycol (30%)/sodium chloride (1.6 M), and incubated at room temperature for 2 hr. Samples are centrifuged (10,000 g for 20 min) and the partially purified nucleic acid pellet resuspended in 20 ml of TE (10 mM Tris-HCl, 1 mM sodium EDTA, pH 8.0). Potassium acetate (7.5 M) is added to a final concentration of 0.5 M. Samples are transferred to ice for 5 min then centrifuged (16,000 g, 30 min) at 4° C. to precipitate proteins and polysaccharides. The aqueous phase is extracted with phenol/chloroform and chloroform/isoamyl alcohol (reference 9) and DNA was precipitated by adding 0.6 volume isopropanol. After 2 hrs at room temperature, DNA is pelleted by centrifugation (16,000 g for 30 min) and resuspended in TE (1 ml).

Another method of extracting target nucleic acid from a suspect sample includes the use of sonication (modified from reference 2). Extraction buffer (100 ml) is mixed with soil (50 g) on ice. The mixture is sonicated using a High Intensity Ultrasonic Processor (Vibra Cell) with a standard 13 mm horn solid probe for 150 seconds. The sample is cooled in ice and the sonication repeated. SDS was added (10 ml; 20%) and the sample incubated at 65° C. for 1 hr. The sample is transferred to centrifuge bottles (250 ml) and centrifuged at 6000 g for 10 min. The supernatant is collected, and the soil pellet re-extracted with further extraction buffer (50 ml), incubation at 65° C. for 10 minutes and centrifuged as above. Extraction is then continued as per bead beating method.

Another method of extracting target nucleic acid from a suspect sample includes the use of enzymatic lysis (modified from reference 3). Extraction buffer (100 ml) containing proteinase K (5 mg) is mixed with soil (50 g) in 250 ml centrifuge tubes. The sample is incubated at 37° C. for 30 minutes with shaking at 180 rpm. SDS is added (10 ml; 20%) and the sample incubated at 65° C. for 90 min. The supernatant is collected after centrifugation at 6000 g for 10 min at room temperature. Extraction is continued as per bead beating method.

Another method of extracting target nucleic acid from a suspect sample includes DNA extraction from bacterial cells isolated from soil (modified from reference 9 and reference 4). The bacterial fraction of soil is separated from the inorganic or humic layer by a differential centrifugation technique (reference 4). Bacterial cells are lysed using lysozyme and the DNA purified using ammonium acetate precipitation and ethanol precipitation (reference 4). DNA is resuspended in TE.

Another method of extracting target nucleic acid from a suspect sample includes the use of Silica, which is the simplest method. Target nucleic acid will bind to silica in the presence of high concentrations of chaotropic salts (reference 5, reference 6, and reference 7). These salts are then removed with an alcohol-based wash and the target nucleic acid eluted in a low ionic strength solution such as TE buffer or water. The binding of target nucleic acid to silica seems to be driven by dehydration and hydrogen bond formation, which competes against weak electrostatic repulsion (reference 8). Hence, a high concentration of salt will help drive target nucleic acid adsorption onto silica, and a low concentration will release the target nucleic acid.

Another method of extracting target nucleic acid from a suspect sample includes the use of commercially available kits. For example, the Qiagen genomic-tip, QUIamp UltraSens virus kit, or DNaesy Tissue Kit may be used. Alternatively the Sigma Gen Elute Bacterial genomic DNA kit, or Promega products such as Wizard genomic DNA purification or SV Total RNA extraction kits may also be used.

Labeling of Target Nucleic Acid

There is a variety of direct methods to label target nucleic with dyes or chromatic substances that produce colors in the visible region of the spectrum or various degrees of blackness, preferably producing signals observable at the naked eye. Among all the methods, direct labeling of target nucleic acids with florescent dyes (particularly 6-FAM with excitation in the ultraviolet at 290-330 nm and emission in the visible at 595 nm) is preferred. Other fluorescent molecules can be used without departing from the intent of the disclosure. As an example, digoxigenin (DIG)-labeled nucleotides were incorporated during PCR amplification (FIGS. 4 and 5). This approach is specific, sensitive, and therefore desirable.

Other labeling approaches include methods employing indirect labeling of target nucleic acids by employing a secondary binding by antibodies, secondary nucleic acid probes, or other binding systems like avidin-streptoavidin. It is preferred that labeling of target nucleic acids derived from biological threat agents is performed by hybridization to a secondary probe labeled with florescent molecule or DIG. The secondary probe was designed with a sequence still complementary to the target genome but at a difference location and hence of different sequence than the capture nucleic acid. In this approach, we attached the specific capture nucleic acid to the membrane, hybridized the target nucleic acid to the capture nucleic acid, and then hybridized the secondary labeled probe to the immobilized target nucleic acid sequence. In the absence of target nucleic acid, the labeled secondary probe is easily washed away and the membrane remains clean without apparent signal. When the target nucleic acid is captured on the solid support such as a membrane (i.e., the target nucleic acid is bound to the capture nucleic acid), the secondary probe with label is not washed away and a distinctive signal is perceived by the naked eye at the location where the capture nucleic acid was spotted on the solid support. This method can be accomplished by soldiers or emergency response personnel.

Hybridization of Target Nucleic Acid with Capture Nucleic Acid

Hybridization between target nucleic acid and capture probe is based on the physicochemical attraction between complementary bases (pyrimidine-purine) in nucleic acids. That is, adenine binds to thymidine (DNA) or uridine (RNA), and cytosine binds to guanosine. The hybridization is thermodynamically favored within a range of temperature and therefore spontaneous (does not need outside energy). There are fine technical variations on temperature or hybridization time and addition of solvents, detergents, or substances that speed hybridization by reducing the reaction volume or increasing hybridization kinetics. However, hybridization of target nucleic acid to capture probe consist largely of denaturation (unfold the sequence to make it available for hybridization) involving heating and rapid cooling, followed by hybridization below a selected temperature (melting temperature or Tm) below which there is stable binding of the sequences of target and probe. Each complementary pair of target and probe have a specific Tm depending on the composition of bases. The challenge in multiplex or simultaneous hybridization is to select target nucleic acid and capture nucleic acid with compatible hybridization characteristics and to discover similar hybridization conditions for all pairs simultaneously (Tm, and requirements for solvents, detergents, and other adjuvant substances).

A range of hybridization conditions can be used depending on the stringency required with hybridization temperatures ranging from 5° C. to 70° C., preferably between 15° C. and 55° C., and more preferably between 30 and 52° C. Hybridization conditions also can be varied within two units of pH around neutral pH 7.0, preferably between pH 6.5 and 7.8, more preferable at ph 7.4. Buffer and buffer concentrations that work include a) between 0.5× to 20×SCC (20×SCC is 175.3 g/l of NaCL, 27.6 g/l NaH2PO$_4$, and 7.4 g/l EDTA, pH 7.4), b) 40 mM PIPES (pH 6.4), 1 mM EDTA (pH 8.0), 0.4M NaCl, and 80% formamide; or c) 50 mM KCl, 10 mM Tris-Cl pH 8.3 and 1.5 mM MgCl$_2$. Other buffers salts can be used with similar results.

A detergent such as SDS (0.1 to 1%), or Triton, Tweeen, or NP-40 (at concentrations between 0.1% and 5%) can be used to facilitate wetting membranes and hybridization. Formamide (between 20 and 80%) or/and other adjuvants like dextran sulfate (between 1% and 15%), Ficoll (Type 400 Pharmacia, between 0.5 and 5%), polyvylpyrrolidone (between 0.5 and 5%), protein [in the range between 0.05% and 5%, or bovine serum albumin (BSA), preferably at concentrations of 8 ug/ul, or dry milk in the range of 1% and 10%], DMSO (dimethyl sulfoxide), between 5 and 10%, glycerol (5-10%), and/or heparin (between 50 and 500 micrograms/ml) can be included to lower hybridization temperature, decrease background, or to speed hybridization. Non-specific nucleic acid, like salmon sperm DNA, calf thymus DNA, herring sperm DNA, calf liver DNA, or other nucleic acid is useful if placed in the hybridization mixture to reduce/block non-specific binding of target to the membrane.

Using the Invention

In addition, the methods and products of the present invention are able to detect biological threat agent without amplification of target nucleic acid. Biological threat agents including viruses and bacteria present in powders or other environmental samples would be in large amounts (i.e., 2 to 3 micrograms or more) during, or after, a terrorist attack. Nucleic acid extraction methods will be able to release large amounts of target nucleic acid from suspect samples. Unlike clinical samples, where PCR amplification is needed due to the low amounts of infectious agent in clinical specimens, the amounts of threat agent found in powders and other environmental samples taken from a combat situation will be detected by the detection methods and devices of the present invention without the need for amplification of the target nucleic acid by PCR.

The biological threat agents detected by the methods and devices of the present invention are based on the specific capture nucleic acid sequences bound to the solid support. A soldier, or operator, will choose a solid support bound with the capture nucleic acid sequences specific to the biological threat agents one wishes to detect in a suspect sample. An operator of the product is able to identify one or more biological threat agent(s) in a suspect sample by simply inserting the solid support into the sample. The detection device and methods of the present invention will identify biological threat agents upon visual inspection of the solid support. It is preferred that the disclosed detection device and methods of the present invention include PCR amplification of target nucleic acid when the suspect samples contains approximately $2\times10^2$ target nucleic acid sequences or less. Typically, in a combat situation or during a civilian threat situation, the amount of biological agent in a suspect sample is large. A suspect sample in such a situation may contain $1\times10^8$ target nucleic acids or greater. Hybridization of digoxigenin labeled amplified target nucleic acids by PCR is observable to the naked eye on the detection device of the present invention as shown in FIGS. 6, 7 and 8

EXAMPLES

Example 1

Virus strains: Viruses used in this study included vaccinia virus (VAC) strain Modified Vaccinia Ankara, Venezuelan equine encephalomyelitis virus (VEE) strain TC-83, Western equine encephalomyelitis virus (WEE) strain California, Sindbis virus (SIN) strain Ar-339, and Fort Morgan virus (FMV) strain CM4-146. VAC, SIN, WEE and FMV were purchased from the American Type Culture Collection (Manassas, Va.). VEE was provided by Dr. Mike Parker of USAMRIID, Fort Detrick, Md. Viruses were grown and titrated on Vero (African Green Monkey Kidney) cells or BHK (Baby Hamster Kidney) cells. To prepare virus stocks, cells present in the cell culture supernatants were removed by centrifugation and the supernatants were stored at −80° C. until used for nucleic acid extraction.

Oligonucleotides: Oligonucleotides used in this study are listed in FIGS. 1 and 2, amplicon sizes are listed in FIG. 3. Oligonucleotides used as primers in RT-PCR reactions for amplification of alphaviral sequences (cM3W and M2W-A) were targeted to the alphavirus non-structural protein 1 (NSP1) gene. Primer cM3W was developed by Pfeffer et al (Am. J. Trop. Med. Hyg. 57, 709-718, 1997), primer M2W-A is similar to the primer M2W described by Pfeffer et al. (above) but lacks the two 3' nucleotides of M2W. The remaining sequences in FIG. 1 were selected after computational analysis for specificity to the threat agent and compatibility with a multiplex format.

PCR and RT-PCR: DNA or RNA was prepared from cell culture supernatants using the Ultrasensitive Virus Kit (Qiagen, Inc., Valencia, Calif.) and stored at −80° C. until used for amplification. PCRs and RT-PCRs were performed using the Accessquick RT-PCR kit (Promega, Madison, Wis.). Reactions included Accessquick master mix (final concentration 1×), RT and PCR primers at a final concentration of 1 pmol/ul and 5 μl of sample RNA or DNA in a final volume of 50 μl. One microliter of AMV reverse transcriptase was added to RT-PCR tubes. PCR tubes were prepared similarly except that AMV reverse transcriptase was not added to the tubes. Tubes were placed in a thermalcycler and subjected to the following program: 48° C. for 45 min (reverse transcription step), 95° C. for 2 min, 35 cycles consisting of incubation at 95° C. for 30 seconds, 40° C. for 1 minute, and 72° C. for 1 minute, then 72° C. for 5 min. Tubes were stored at 4° C. until processed. Five microliters of the amplified sample were subjected to electrophoresis through a 2% agarose gel. Amplified DNA was visualized by UV transillumination of the ethidium bromide stained gels. Amplified DNA was purified using the PCR Purification Kit (Qiagen, Inc., Valencia, Calif.).

Macroarrays:

a) Initial macroarrays consisted of spot blots produced on nylon membranes using a 96-well Minifold apparatus (Schleicher and Schuell, Keene, N.H.). Capture oligonucleotides spotted on the membranes were diluted to a final concentration of 5 pmol/μl in 10×SSC buffer. Blotter paper was cut to Minifold size, soaked in 10×SSC and placed on the Minifold. A Supercharge Nylon membrane (Schleicher and Schuell, Keene, N.H.) was soaked in 10×SSC and placed on top of blotter paper. The membrane was clamped into place on the Minifold and oligonucleotides were added to the wells. Each oligonucleotide was added to multiple wells of one 12-well row, 50 μl per well. SSC alone was added to wells serving as negative controls. Vacuum was applied to the Minifold for about 20-30 seconds. The membrane and blotter paper were removed, placed on another piece of pre-wet (in 10×SSC) blotter paper and the membrane was cross-linked on the autolink setting in a Stratalinker (Stratagene, La Jolla, Calif.). The membrane was removed from the Stratalinker and cut into strips, each strip carrying each of the capture oligonucleotides. The strips were air-dried and stored at room temperature in the dark.

b) Later macroarrays were produced using a macroarraying tool (V&P Scientific, San Diego, Calif.). To produce a source plate for the macroarray, capture oligonucleotides were first diluted to 50 pm/μl in sterile water, and then 100 μl were added to the wells of a 96-well plate containing 50 μl of 20×SSC. The final concentration of capture oligonucleotide in each well was 33 pm/μl, the final concentration of SSC was 6.7×. Water was added to wells serving as negative controls.

Capture oligonucleotides were added to the wells as follows:

| Column | |
| --- | --- |
| 1 | 2 |
| Neg | Neg |
| OPHA-1 | VEE-1 |
| CM3W | WEE-1 |
| HA-VAC | EEE-1 |
| HA-VAR | SIN-1 |
| HA-COW | FMV-1 |

-continued

| Column | |
| --- | --- |
| 1 | 2 |
| HA-CML | Neg |
| Neg | Neg |

These 2 columns carried all of the capture oligonucleotides. In the source plate, this pattern was repeated every 2 columns (column 3=Column 1, column 4=column 2 and so on). Each membrane was stamped with a 96-well replicator, UV crosslinked, dried, and cut into 6 strips, each strip carrying 2 columns arrayed as shown above for column 1 and 2.

For array stamping, four pieces of supercharged nylon membrane were arranged on top of blotter paper. Multi-print frames were arranged on the membranes. Membranes were marked across the width of the upper inside of the filters to indicate the top and to keep the frame oriented correctly. An additional mark was made after every 2 columns for later cutting. The pins on the 3 μl replicator (V&P Scientific, San Diego, Calif.) were rinsed once in pin cleaner, twice in sterile water, once in isopropyl alcohol and were then allowed to air dry. The replicator pins were placed into the source plate using the guide pinholes. The replicator was removed slowly and placed into the frame over a membrane using the pinhole guides. The stamping was repeated 3 times for each membrane. The membranes were placed on a piece of pre-wet (in 10×SSC) blotter paper and were cross-linked on the autolink setting in a Stratalinker (Stratagene, La Jolla, Calif.). The membranes were removed from the Stratalinker and cut into strips, each strip carrying each of the capture oligonucleotides. The strips were air-dried and stored at room temperature in the dark.

Hybridizations: The DIG labeling and detection kit (Roche Diagnostics Corporation, Indianapolis, Ill.) were used for this procedure. PCR products were first labeled with digoxigenin for colorimetric detection. Amplified DNA was purified with the PCR Purification Kit (Qiagen, Inc., Valencia, Calif.) and one-half of the purified PCR (or RT-PCR) product (approximately 200 ng in 15 μl of water) was denatured at 100° C. for 10 minutes and quick cooled on ice for 5 minutes. Four μl of DIG-High Prime was added and the mixture was incubated at 37° C. for 3 hours. To stop the reaction, 2 μl of 0.2 M EDTA was added. Macroarray strips were pre-hybridized in 6 ml DIG Easy Hyb for at least one hour at 40° C. in a 15 ml tube on a rotator in a hybridization oven.

An aliquot (approximately one half) of the labeled PCR product was denatured at 100° C. for 5 minutes and quickly cooled on ice for 5 minutes. The mixture was added to 2 ml of DIG Easy Hyb in a 15 ml tube. After pre-hybridization, the macroarray strip was added to the tube containing the labeled PCR product. Hybridizations were carried out overnight at 40° C. on a rotator in a hybridization oven. Washings were carried out in the 15 ml tube used for the hybridization. Strips were washed twice for 5 minutes each in 2×SSC, 0.1% SDS at room temperature with gentle agitation, and twice for 15 minutes each in 0.5×SSC, 0.1% SDS at 40° C. with gentle agitation. For immunologic detection the strips were washed according to the manufacturer (DIG detection kit, Roche Diagnostics Corporation, Indianapolis, Ill.) for 2 minutes in 5 ml washing buffer, then incubated for 30 minutes in 5 ml blocking solution, 30 min in 5 ml antibody solution, twice for 15 minutes each in 5 ml washing buffer, 2 min in 5 ml detection buffer and for approximately 2 hours in 5 ml color substrate solution or until color was evident. Strips were then washed in 5 ml water, dried and either inspected with the naked eye or photographed. Please observe FIGS. 6, 7, and 8.

Densitometry: Arrays that had faint signal as observed with the naked eye were densitometrically scanned using AlphaEase FC software (Alpha Innotech Corporation, San Leandro, Calif.). Photographic images of the macroarrays after hybridization were overlaid with arrays of circles surrounding the area occupied by each capture oligonucleotide. The dots corresponding to detected signal were then scanned. The values obtained from the scans represent the average pixel values within the circles, adjusted to a scale of 0 to 100 (0 corresponding to white pixel values and 100 corresponding to black pixel values).

Amplification of Orthopoxvirus and Alphavirus Sequences: Viral gene sequences were first amplified from cell culture supernatants in which the viruses had been grown. Viral nucleic acids were extracted from culture supernatants containing approximately a total of $8 \times 10^4$ virus plaque forming units (PFU). The kit was used for the extraction of both RNA and DNA.

Initial experiments utilizing only the orthopox-specific amplification primers OPHA-1 and OPHA-2 or OPTK-1 and OPTK-2 demonstrated that they amplified DNA fragments of the correct size from samples containing VAC DNA, but not from negative control samples containing FMV RNA or from samples of Vero or BHK conditioned media. Amplification occurred in the presence and absence of AMV reverse transcriptase.

Experiments utilizing only the alphavirus-specific amplification primers M2W-A and cM3W resulted in the amplification of DNA fragments of the correct size only from samples of FMV RNA, but not from VAC DNA or from Vero or BHK conditioned media. Amplification occurred in the presence, but not in the absence of AMV reverse transcriptase.

Multiplex RT-PCR utilizing both *orthopox*- and alphavirus-specific primers (OPHA1 and OPHA2, M2W-A and cM3W) yielded amplification of DNA corresponding to the size of the orthopoxvirus fragment from the VAC sample and DNA corresponding to the size of the alphaviral fragment from the FMV sample. Multiplex RT-PCR utilizing the orthopox- and alphavirus-specific primers (OPHA3 and OPHA2, M2W-A and cM3W) resulted in amplification of DNA fragments corresponding to the size of the alphaviral fragment from FMV, SIN, WEE and VEE RNA samples and amplification of a DNA fragment corresponding to the size of the orthopoxvirus fragment from the VAC DNA sample. Please observe FIGS. 4 and 5.

Detection of Sequences by Macroarray:

After comparison of various labels, digoxigenin labeling resulted in colorimetric hybridization results easily observable with the naked eye. Therefore, macroarray strips were prepared and used with digoxigenin labeled PCR products. These strips carried capture oligonucleotides identical to one of the amplification primers for orthopoxvirus amplification and one identical to the amplification primer for the alphaviruses. Hybridization to these capture oligonucleotides indicates amplification of *orthopox* or alphaviral sequences. The strips also carried capture oligonucleotides that would bind specifically DNA amplified from any of 5 alphaviruses and Cowpox virus, and oligonucleotides specific for a subset of orthopoxviruses (i.e., oligonucleotides listed in FIGS. 1 and 2). The hybridization pattern on the macroarray serves to identify presumptively each of the 5 alphaviruses and each of the 4 orthopoxviruses. VAC DNA amplified with OPHA-2 and OPHA-3 primers was labeled with digoxigenin and hybridized to a macroarray strip. Spots were observed on the strip corresponding to positions of the array carrying the capture oligonucleotides OPHA-1 (generic for orthopoxvirus PCR product) and HA-VAC (specific for vaccinia virus). Although most vaccinia virus strains carry sequences identical to the camelpox-specific oligonucleotide (HA-CML; see Table 1), vaccinia strain MVA has a one-base mismatch with this sequence, which apparently prevented hybridization with the HA-CML capture oligonucleotide. Digoxigenin labeled RT-PCR product amplified from VEE RNA (extracted from approximately $2 \times 10^4$ virus PFU) bound only to spots corresponding to positions carrying the oligonucleotides cM3W (generic for Alphaviruses) and VEE-1 (specific for VEE).

Since variola major virus DNA was not available for testing the macroarray strips, a small portion of variola DNA was constructed by PCR. Two oligonucleotides of 50 nucleotides each were produced with a 10-base overlap at their 3' ends. Each oligonucleotide matched all 3 variola sequences, but not other orthopoxviruses, in an alignment of orthopoxvirus HA genes. These two oligonucleotides were subjected to PCR amplification, resulting in a 90-bp fragment of variola DNA. When labeled with digoxigenin and hybridized to a macroarray strip the 90-bp fragment bound only to the spot corresponding to the variola-specific capture oligonucleotide HA-VAR (FIG. 4C). Binding of the 90-bp fragment to the HA-VAR spot was improved by reduction of the hybridization temperature to 35° C.

Although the present invention has been described in detail with reference to examples above, it is understood that various modifications can be made without departing from the spirit of the invention. Accordingly, the invention is limited only by the following claims. All cited patents, patent applications and publications referred to in this application are herein expressly incorporated by reference in their entirety. Please see FIGS. 6, 7 and 8.

REFERENCES

1—Yeates C, Gillings M R, Davison A D, Altavilla N, Veal D A. PCR amplification of crude microbial DNA extracted from soil. *Letters in Applied Microbiology* 1997; 25:303-307.

2—Picard C, Ponsonnet C, Paget E, Nesme X, Simonet P. Detection and enumeration of bacteria in soil by direct DNA extraction and polymerase chain reaction. *Applied and Environmental Microbiology* 1992; 58:2717-2722.

3—Zhou J, Bruns M A, Tiedje J M. DNA recovery from soils of diverse composition. *Applied and Environmental Microbiology* 1996; 62:316-322.

4—Steffan R J, Atlas R M. DNA amplification to enhance detection of genetically engineered bacteria in environmental samples. *Applied and Environmental Microbiology* 1998; 54:2185-2191.

5—Chen, C. W. and Thomas, C. A. Jr. (1980) Recovery of DNA segments from agarose gels. *Anal. Biochem.* 101, 339-41.

6—Marko, M. A. et al. (1982) A procedure for the large-scale isolation of highly purified plasmid DNA using alkaline extraction and binding to glass powder. *Anal. Biochem.* 121, 382-7.

7—Boom, R. et al. (1990) Rapid and simple method for purification of nucleic acids. *J. Clin. Microbiol.* 28, 495-503.

8—Melzak, K. A. et al. (1996) Driving forces for DNA absorption to silica in perchlorate solutions. *J. Colloid Interface Sci.* (*USA*) 181, 635-44.

9—Sambrook J, Fritsch E F, Maniatis T. Molecular cloning—a laboratory manual. Cold Spring Harbor, USA, Cold Spring Harbor Laboratory Press; 1987.

---

What is claimed is:

1. A method of detecting a biological threat agent, comprising the steps of:
   (a) extracting target nucleic acid from a suspect sample;
   (b) labeling said target nucleic acid to produce labeled target nucleic acid;
   (c) exposing said labeled target nucleic acid to capture nucleic acid, wherein said capture nucleic acid comprises a plurality of individual nucleic acid sequences bound to a solid substrate, and wherein each of said individual nucleic acid sequences is positioned at a specific location on said solid substrate, wherein said capture nucleic acid comprising a plurality of individual nucleic acid sequences comprises the nucleotide sequences consisting of SEQ ID NOS: 1-48; and
   (d) determining the presence of a biological threat agent by reading a signal emitted by said labeled target nucleic acid after it attaches to one or more of said capture nucleic acids at specific locations on said substrate; wherein said reading a signal consists of visual inspection by the naked eye.

2. The method of claim 1, wherein the biological threat agent is selected from the group consisting of an alphavirus, orthopoxvirus, filovirus, bunyavirus, flavivirus, paramyxovirus, *Bacillus anthracis, Yersinia, Francicella tularensis, Brucellas, E. coli* 0157:117, *Burkholderias, Coxiella burnetti, Rickettsias* or a combination thereof.

3. The method of claim 1, wherein said labeling comprises attaching a label selected from the group consisting of visible, UV, IR fluorescent, radioactive, mass, and electrochemical labels.

4. The method of claim 3, wherein the label comprises digoxigenin.

5. The method of claim 1, wherein before labeling the target nucleic acid is amplified by polymerase chain reaction using primer sets comprising SEQ ID NOS: 1-48.

6. A method of detecting a biological threat agent, comprising the steps of:
   (a) extracting target nucleic acid from a suspect sample;
   (b) exposing said target nucleic acid to capture nucleic acid, wherein said capture nucleic acid comprises a plurality of individual nucleic acid sequences bound to a solid substrate, and wherein each of said individual nucleic acid sequences is positioned at a specific location on said solid substrate, wherein said capture nucleic acid comprising a plurality of individual nucleic acid sequences comprises the nucleotide sequences consisting of SEQ ID NOS: 1-48;
   (c) labeling said target nucleic acid to produce a labeled target nucleic acid; and
   (d) determining the presence of a biological threat agent by reading a signal emitted by said labeled target nucleic acid after it attaches to one or more of said capture nucleic acids at specific locations on said substrate; wherein said reading a signal consists of visual inspection by the naked eye.

7. The method of claim 6, wherein the biological threat agent is selected from the group comprising an alphavirus, orthopoxvirus, filovirus, bunyavirus, flavivirus, paramyxovirus, *Bacillus anthracis, Yersinia, Francicella tularensis, Brucellas, E. coli* 0157:H7, *Burkholderias, Coxiella burnetti, Rickettsias* or a combination thereof.

8. The method of claim 6, wherein said labeling comprises attaching a label selected from the group consisting of visible, UV, IR fluorescent, radioactive, mass, and electrochemical labels.

9. The method of claim 8, wherein the label comprises digoxigenin.

10. The method of claim 6, wherein before exposing said target nucleic acid to capture nucleic acid, the target nucleic acid is amplified by polymerase chain reaction using primers sets comprising SEQ ID NOS: 1-48.

11. A method of detecting a biological threat agent, comprising the steps of:
   (a) extracting target nucleic acid from a suspect sample;
   (b) labeling said target nucleic acid with a chromatic substance to produce a labeled target nucleic acid;
   (c) exposing said labeled target nucleic acid to capture nucleic acid, wherein said capture nucleic acid comprises a plurality of individual nucleic acid sequences bound to a solid substrate, and wherein each of said individual nucleic acid sequences is positioned at a specific location on said solid substrate, wherein said capture nucleic acid comprising a plurality of individual nucleic acid sequences comprises the nucleotide sequences consisting of SEQ ID NOS: 1-48; and
   (d) determining the presence of a biological threat agent by reading a signal emitted by said labeled target nucleic acid after it attaches to one or more of said capture nucleic acids at specific locations on said substrate; wherein said reading a signal consists of visual inspection by the naked eye.

12. The method of claim 11, wherein the biological threat agent is selected from the group consisting of an alphavirus, orthopoxvirus, filovirus, bunyavirus, flavivirus, paramyxovirus, *Bacillus anthracis, Yersinia, Francicella tularensis, Bru-*

*cellas, E. coli* 0157:H7, *Burkholderias, Coxiella burnetti, Rickettsias* or a combination thereof.

13. The method of claim 11, wherein the visual inspection by the naked eye comprises identification of colors on the solid substrate.

14. The method of claim 11, wherein before labeling the target nucleic acid is amplified by polymerase chain reaction using primer sets comprising SEQ ID NOS: 1-48.

* * * * *

SEQUENCE LISTING

<160> NUMBER OF SEQ ID NOS: 48

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ttgttatgag tgcttggtat aaggagcc                                       28

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
caattccaga tgatgtactt actgtagtgt atgag                               35

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
caatactttt gttactaata tcattagtat                                     30

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ataatcggcc ccatgttttc agg                                            23

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ggctactata actattttc cttcgtttgc c                                    31

<210> SEQ ID NO 6
<211> LENGTH: 25
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 6
ctacacatac atctaaaaaa atagg                                          25

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
tgataaagaa gaagatcata cagtc                                          25

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
tcctcagaca tctaaaaaaa tagg                                           24

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
tcctcagaca cagatatcta aaaa                                           24

<210> SEQ ID NO 10
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
tcattagtat actctacacc ttatcctcag acacagatat ctaaaaaaat               50

<210> SEQ ID NO 11
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tatattattt ctactacatg atagagttgc atcatcacct atttttttag               50

<210> SEQ ID NO 12
<211> LENGTH: 30
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: a, c, g, t, unknown or other
<220> FEATURE:
<221> NAME/KEY: modified_base
<222> LOCATION: (11)..(11)
<223> OTHER INFORMATION: a, c, g, t, unknown or other
<220> FEATURE:
<221> NAME/KEY: modified_base
<222> LOCATION: (14)..(14)
<223> OTHER INFORMATION: a, c, g, t, unknown or other
<220> FEATURE:
<221> NAME/KEY: modified_base
<222> LOCATION: (23)..(23)
<223> OTHER INFORMATION: a, c, g, t, unknown or other

<400> SEQUENCE: 12
acatraankg ngtngtrtcr aanccdaycc                                   30

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
yagagcdttt tcgcaystrg c                                            21

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
tgatcgaaac ggaggtggac ccatccga                                     28

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tcattgagag cgaagtcgac cgggacca                                     28

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tcattgaggg agaagtggat acagacca                                     28

<210> SEQ ID NO 17
<211> LENGTH: 28
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 17
ttatagaaag cgaagtcgac cgggaaca                                          28

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
taatcgagct ggaggttcct accacagc                                          28

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
tggatttcaa gttgtactgg accgat                                            26

<210> SEQ ID NO 20
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tgtcacggtc tggaaccgta ggtcca                                            26

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tgctgaccaa tctaagcctg cgtt                                              24

<210> SEQ ID NO 22
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
agcaaactgc tcagtacgat caacgc                                            26

<210> SEQ ID NO 23
<211> LENGTH: 26
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 23
acccacctca ttggctatgg cggcgt                                              26

<210> SEQ ID NO 24
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
tcacgcggga tgtgatactc cggcgt                                              26

<210> SEQ ID NO 25
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
agccactttt gcaatcgctg tgtgag                                              26

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
agctgcgatt agttctgagc ctcggt                                              26

<210> SEQ ID NO 27
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
tgccattgcc ctgtcatttg ccgcag                                              26

<210> SEQ ID NO 28
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
acaactgact gaacagactc aggtcg                                              26

<210> SEQ ID NO 29
<211> LENGTH: 22
<212> TYPE: DNA
<213> ORGANISM: Artificial Sequence
<220> FEATURE:
```

-continued

```
<223> OTHER INFORMATION: Description of Artificial Sequence: Synthetic
      oligonucleotide

<400> SEQUENCE: 29
ttacttgtct gcggcgcctt gg                                              22

<210> SEQ ID NO 30
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
taggctcctc cccacat                                                    17

<210> SEQ ID NO 31
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
cgatggcgtc atccatgtgc tgggtg                                          26

<210> SEQ ID NO 32
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
agtttgagca tgatgccgac gaaagc                                          26

<210> SEQ ID NO 33
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
gcaggcctga actcatcgtc ggatga                                          26

<210> SEQ ID NO 34
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
tcatcccaat acgagcggtc gctggt                                          26

<210> SEQ ID NO 35
<211> LENGTH: 26
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 35
gcagcaccgt atacaccacc caatgg                                                           26

<210> SEQ ID NO 36
<211> LENGTH: 26
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 36
acgtctccaa cagacgtgtg tccgga                                                        26

<210> SEQ ID NO 37
<211> LENGTH: 26
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 37
acactacatc ctttggtgcg gacctc                                                       26

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 38
tttctcgttt ctggctgagg acggc                                                         25

<210> SEQ ID NO 39
<211> LENGTH: 26
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 39
gggttcagtt agcctctcac tggacg                                                      26

<210> SEQ ID NO 40
<211> LENGTH: 26
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 40
aggcggcatc acaagatacg gctgct                                                      26

<210> SEQ ID NO 41
<211> LENGTH: 25
<212> TYPE: DNA
<213> ORGANISM: Artificial Sequence
<220> FEATURE:
<223> OTHER INFORMATION: Description of Artificial Sequence: Synthetic
    oligonucleotide

```
<400> SEQUENCE: 41
tggcagccat caaaagggtg gaatg                                              25

<210> SEQ ID NO 42
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
tccaatcagt gatccgcaca gcttg                                              25

<210> SEQ ID NO 43
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
agtgactgct ccagatacag ccgagg                                             26

<210> SEQ ID NO 44
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
tgttgagagc acccatggat cggtcg                                             26

<210> SEQ ID NO 45
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
cccaacgaaa ccttgcgtga ggcat                                              25

<210> SEQ ID NO 46
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
aaacgtctcg cttaaactca acgacg                                             26

<210> SEQ ID NO 47
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 47
gcttatttta gaggttatag agttcg                                          26

<210> SEQ ID NO 48
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
acttcttgag gtaaaagtaa agctc                                           25
```